(12) United States Patent
Shanmuganathan et al.

(10) Patent No.: US 11,109,589 B2
(45) Date of Patent: Sep. 7, 2021

(54) PROCESS FOR PREPARING A HOMOGENEOUS SOLUTION OF A POLYMER AND MELANIN

(71) Applicant: COUNCIL OF SCIENTIFIC & INDUSTRIAL RESEARCH, New Delhi (IN)

(72) Inventors: Kadhiravan Shanmuganathan, Pune (IN); Nikhil Kamlakar Pimpalkar, Pune (IN); Abhijit Pravin Shete, Pune (IN); Farsa Ram, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 224 days.

(21) Appl. No.: 16/307,617

(22) PCT Filed: Jun. 8, 2017

(86) PCT No.: PCT/IN2017/050232
§ 371 (c)(1),
(2) Date: Dec. 6, 2018

(87) PCT Pub. No.: WO2017/212500
PCT Pub. Date: Dec. 14, 2017

(65) Prior Publication Data
US 2019/0297880 A1    Oct. 3, 2019

(30) Foreign Application Priority Data
Jun. 9, 2016   (IN) .............................. 201611019780

(51) Int. Cl.
*A01N 25/10* (2006.01)
*A01N 43/90* (2006.01)
(Continued)

(52) U.S. Cl.
CPC ............. *A01N 25/10* (2013.01); *A01N 43/90* (2013.01); *A61K 8/65* (2013.01); *A61K 8/72* (2013.01);
(Continued)

(58) Field of Classification Search
CPC .......... A01N 25/10; A01N 43/90; A61K 8/72; A61K 8/731; A61K 8/65; A61K 8/96;
(Continued)

(56) References Cited

U.S. PATENT DOCUMENTS 3,102,775 A * 9/1963 Seeger ...................... D01F 6/14
264/185
5,216,116 A   6/1993 Pawelek
(Continued)

FOREIGN PATENT DOCUMENTS

KR   20160072590 A * 6/2016
WO   2001/085104 A1   11/2001
(Continued)

OTHER PUBLICATIONS

Synergistic effect of quaternary ammonium hydroxide and crown ether on the rapid and clear dissolution of cellulose at room temperature, by Tadashi Ema et al., RSC Adv., 2014, vol. 4, p. 2523-2525, published Dec. 9, 2013 (https://pubs.rsc.org/en/content/articlelanding/2014/ra/c3ra45888a#!divAbstract) (Year: 2013).*

(Continued)

*Primary Examiner* — Leith S Shafi
*Assistant Examiner* — Inja Song
(74) *Attorney, Agent, or Firm* — Ladas & Parry LLP

(57) ABSTRACT

The present invention discloses a process for preparing a homogeneous solution of a polymer and melanin. The present invention further discloses a process for preparation of fibers and films from said homogeneous solution.

7 Claims, 6 Drawing Sheets

(51) Int. Cl.
*D01D 1/02* (2006.01)
*D01D 10/06* (2006.01)
*D01F 1/02* (2006.01)
*A61K 8/72* (2006.01)
*A61K 8/73* (2006.01)
*A61Q 17/04* (2006.01)
*A61K 8/65* (2006.01)
*A61K 8/96* (2006.01)

(52) U.S. Cl.
CPC ............... *A61K 8/731* (2013.01); *A61K 8/96* (2013.01); *A61Q 17/04* (2013.01); *D01D 1/02* (2013.01); *D01D 10/06* (2013.01); *D01F 1/02* (2013.01)

(58) Field of Classification Search
CPC ............ A61K 31/403; A61K 31/74–80; A61Q 17/04; D01D 1/02; D01D 10/06; D01F 1/02; C07D 487/06; C07C 211/63
See application file for complete search history.

(56) References Cited

U.S. PATENT DOCUMENTS

| | | | |
|---|---|---|---|
| 5,380,359 A | 1/1995 | Honda et al. | |
| 5,384,116 A | 1/1995 | Pawelek et al. | |
| 5,571,700 A | 11/1996 | Junino et al. | |
| 5,958,387 A | 9/1999 | Baru et al. | |
| 6,315,988 B1 | 11/2001 | Mani et al. | |
| 8,512,685 B2 | 8/2013 | Kelton et al. | |
| 8,586,090 B2 | 11/2013 | Dadachova et al. | |
| 2002/0100725 A1 | 8/2002 | Lee et al. | |
| 2009/0110772 A1* | 4/2009 | Verkade | C08B 5/00 426/48 |
| 2010/0015097 A1* | 1/2010 | Lapina | B01J 20/3085 424/93.4 |
| 2014/0360237 A1 | 12/2014 | Popa et al. | |
| 2018/0110809 A1* | 4/2018 | Carllni | A61K 31/435 |

FOREIGN PATENT DOCUMENTS

| | | |
|---|---|---|
| WO | 2003/011216 A2 | 2/2003 |
| WO | 2008/006186 A2 | 1/2008 |
| WO | 2014/190325 A1 | 11/2014 |

OTHER PUBLICATIONS

English translation of KR-20160072590-A (Year: 2016).*
Singh et al. (Green Chem., 2019, 21, 3328; "Multi-tasking hydrated ionic liquids as sustainable media for the processing of waste human hair: a biorefinery approach," published on May 10, 2019). (Year: 2019).*
International Search Report (ISR) for International Application No. PCT/IN2017/050232.
Written Opinion (WO) for International Application No. PCT/IN2017/050232 dated Sep. 4.
Tadashi Ema et al.; "Supplementary Information Synergistic effect of quaternary ammonium hydroxide and crown ether on the rapid and clear dissolution of cellulose at room temperature", (Dec. 9, 2013), URL: http://www.rsc.org/suppdata/ra/c3/c3ra45888a/c3ra45888a. pdf, (Sep. 4, 2017), XP055403431 [Y] 1-10 * the whole document *.
Daniel R. Dreyer, et al.; Elucidating the Structure of Poly(dopamine); Langmuir 2012; 28; 6428-6435.
Atsushi Oikawa, et al.; Quantitative measurement of melanin as tyrosine equivalents and as weight of purified melanin; Yale Journal of Biology and Medicine, 46, 1973, pp. 500-507.
Mitsuru Abe, et al.; Maintenance-free cellulose solvents based on onium hydroxides: ACS Sustainable Chemistry and Engineering; 2015, 3 (8); pp. 1771-1776.
Krystyna Stepien, et al.; Melanin from epidermal human melanocytes: Study by pyrolytic GC/MS published in Journal of the American Society for Mass Spectrometry, 2009, 20(3), pp. 464-468.
S.N. Deziderio, et al.; Thin films of synthetic melanin; published in Journal of Non-Crystalline Solids, 2004, 338-340,pp. 634-638.
Kadhiravan Shanmuganathan, et al.; Thermooxidativestabilization of polymers using natural and synthetic melanins; published in Macromolecules, 2011, 44 (24), pp. 9499-9507.
Erika S. Bronze-Uhle, et al.; Synthesis and characterization melanin in DMSO; published in Journal of Molecular Structure, vol. 1047, p. 102-108.
Mitsuru Abe, et al.; Fast and facile dissolution of cellulose with tetrabutylphosphonium hydroxide containing 40 wt% water: published in Chemical Communications, 2012, 1808-1810.

* cited by examiner

PROCESS FOR PREPARING A HOMOGENEOUS SOLUTION OF A POLYMER AND MELANIN

RELATED APPLICATION

This application is a national phase entry under 35 USC 371 of International Patent Application No.: PCT/IN2017/050232 filed on 8 Jun. 2017, which claims priority from Indian Application No. 201611019780 filed on 9 Jun. 2016, the disclosures of which are incorporated in their entirety by reference herein.

FIELD OF THE INVENTION

The present invention provides a process for preparing a homogeneous solution of a polymer and melanin.

BACKGROUND AND PRIOR ART OF THE INVENTION

Melanin is a natural biopolymer that is found in most organisms including plants, fungi, animals and even bacteria. Two most common forms of melanin are eumelanin and pheomelanin. Melanins offer a unique suite of physical and chemical properties including photoprotection (absorption of UV radiation and dissipation into harmless heat), photoconductivity, metal-ion chelation, thermoregulation and free-radical quenching. Melanins constitute a class of biomacromolecules that are abundant in nature. Although they exhibit a unique range of physical and chemical properties, their intractable nature precluded their dissolution in common solvents and further processing into functional materials.

Melanin also exhibits anti-bacterial properties, assuming a significant line of defense in human immune system. Other interesting aspects of melanin include its significant structural contribution to the mechanical integrity of the jaws of marine worms and the gradient mechanical stiffness in squid beaks. Notwithstanding the physiological significance of melanins and the voluminous research over the last several decades on different aspects of melanin, how such a complex heterogeneous polymer evolves from simple basic subunits is not yet clear.

Recent attempts to elucidate the structural aspects of melanin using synthetic model systems have resulted in contradictory reports. Solid state CP $^{13}$C NMR experiments on polydopamine (a melanin-like polymer derived by aerobic oxidation of 3-hydroxytyramine hydrochloride (dopamine HCl) in aqueous conditions using tris-(hydroxymethyl)aminomethane (TRIS) as a basic polymerization initiator, indicated the presence of hydrogens bound to the aryl core of the polymer. This led Dreyer et al. to conclude that poly(dopamine) is not covalently bound through aryl-aryl linkages, rather the monomers are held together by strong supramolecular forces such as $\pi$-$\pi$ interactions, charge transfer, and hydrogen bonding.

There are also few reports that suggest multiple levels of structure in natural and synthetic melanins; a primary chemical structure driven by covalent interactions and a secondary structure driven by supramolecular organization. Such a structural postulate is not without precedence. Supramolecular organization in biomacromolecules is known to mediate double helix formation in DNA, secondary and tertiary structure in proteins etc. It has been speculated by several researchers that eumelanins primarily organize into planar oligomeric sheets which further stack through non-covalent interactions to create onion-like nanoaggregates. In fact X-ray scattering studies and high resolution transmission electron microscopy suggests a stacked configuration with an intersheet spacing of 3.7-4.0 Å, analogous to stacking distances in heteroaromatic systems having Π-Π interactions.

U.S. Pat. No. 5,380,359 discloses a melanin-coated pigment which is prepared by coating a carrier with a readily alkali-soluble natural melanin. The readily alkali-soluble natural melanin not only dissolves in aqueous solutions of alkalis such as aqueous ammonia and aqueous solutions of sodium hydroxide, potassium hydroxide and calcium hydroxide, but is also soluble in organic solvents such as triethylamine, triethanolamine, ammonia-containing methanol, ethanol, isopropyl alcohol, propylene glycol, 1,3-butylene glycol, and glycerin, and may be subjected to nonaqueous treatment.

Article titled "Quantitative measurement of melanin as tyrosine equivalents and as weight of purified melanin" by Atsushi Oikawa et al. published in Yale Journal of Biology and Medicine, 1973, 46, pp 500-507 reports a colorimetric method for determination of melanin, using protein-free melanin as standard, and values are compared with those expressed as tyrosine equivalents. For this method, a new procedure was developed to solubilize melanin. Melanins were purified from melanoma tissues and black hair of mice by HCl treatment. This treatment hydrolyzed protein and other macromolecules leaving melanin as insoluble material. These melanin preparations were dissolved in 0.5N dimethyl n-undecyl n-dodecyl ammonium hydroxide in toluene.

WO2003011216 discloses a dissolving agent for melanin and methods of applying such an agent to keratinous fibers. Trialkyl ammonium hydroxide is used to extract melanin pigments from hair, skin or other tissues with the aim of obtaining model melanin for research or diagnostic purposes.

U.S. Pat. No. 5,384,116 discloses synthetic melanin as a sunscreen and tanning agent. A melanin that is soluble in an aqueous solution at a pH between 5 and 9 at a temperature of 0° to 100° C. Mammalian melanins are highly insoluble and can be dissolved (solubilized) only through non-physiological treatments such as boiling in strong alkali, or through the use of strong oxidants such as hydrogen peroxide.

Article titled "Maintenance-free cellulose solvents based on onium hydroxides" by Mitsuru Abe et al. published in ACS Sustainable Chemistry and Engineering, 2015, 3 (8), pp 1771-1776 reports that Tetraalkyl-onium hydroxide aqueous solutions are found to be maintenance-free cellulose solvents, and the 13C NMR measurement is found to be a very useful tool to forecast their cellulose-dissolving ability.

Article titled "Melanin from epidermal human melanocytes. Study by pyrolytic GC/MS" by Krystyna Stepień et al. published in Journal of the American Society for Mass Spectrometry, 2009, 20(3), pp 464-468 reports Pigmentation of human skin is determined by the presence of melanin, the polymeric pigment that is produced in melanocytes and transferred to adjacent keratinocytes. To obtain additional information on the natural pigment structure, the samples were thermally degraded in the presence of tetramethylammonium hydroxide as the derivatizing agent.

WO2008006186 discloses a method of making a sorbent, comprising the steeps of crushing seed husks, acid hydrolysis with extraction of water-soluble ballast substances and formation of the target composition of lignin, cellulose and melanin, water rinsing and drying.

U.S. Pat. No. 5,380,359 discloses a melanin-coated pigment which is prepared by coating a carrier with a readily alkali-soluble natural melanin. The organic pigment consists of an organic compound. A number of dyes and pigments may be used as the organic pigment. In addition, as the inorganic or organic powder may be used resins such as nylon 6, nylon 6.6, nylon powder, and silicon resin, as well as cellulose, crystalline cellulose, silk powder, and the like.

U.S. Pat. No. 5,571,700 discloses process for preparing melanin pigments by bioconversion and use of the pigments obtained in cosmetics. As organic fillers, it is preferable to use particles of polymers derived from keratin, optionally modified, of polymers derived from chitin, optionally deacetylated, of silk fibroin, of synthetic polymers chosen from crosslinked poly(methyl methacrylate) and crosslinked poly-β-alanine, hollow microspheres of copolymers of vinylidine chloride and acrylonitrile or alternatively porous microspheres of polyamide-12, polyamide-6 or of copolyamide-6/12, as well as silicone powders consisting of gums, resins, organopolysiloxane elastomers.

US20140360237 discloses methods for producing melanin, melanin-associated proteins and inorganic fertilizer from fermentation leachates or from nutrient rich solutions spiked with low cost, sugar-rich sources.

U.S. Pat. No. 6,315,988 discloses process for preparing protein-bound melanin and/or peptide bound melanin, and products thereof. The soluble protein- and/or peptide-bound melanin of this invention is useful as a sunscreen and as a coloring and/or flavoring for food.

WO2014190325 discloses compositions including a first silk fibroin layer, and a second silk fibroin layer, wherein at least a portion of the first silk fibroin layer is directly adhered to at least a portion of the second silk fibroin layer to form a silk-silk interface and methods of making the same. The melanin solution was mixed into 6% aqueous silk solution during casting, and the volume casted was adjusted for the decrease in silk concentration, to ensure equivalent film thickness.

U.S. Pat. No. 3,102,775 discloses a process of wet spinning stereoregular polyvinyl alcohol for preparation of fibre.

US20020100725 discloses a method for preparing a thin fiber-structured polymer web suitable for a high-speed and large-scale production using electrospinning. The conventional fiber fabrication technology, i.e., melt spinning, web spinning, dry spinning, or dry jet-wet spinning involves extrusion of a polymer melt or solution through a nozzle by the mechanical force and solidification of it to fabricate fibers.

U.S. Pat. No. 8,586,090 discloses melanin nanoshells and their use for protection against radiation, particularly ionizing radiation, and electronic pulses, and methods of making materials comprising melanin nanoshells. Melanin nanoshells may be used in remediation in connection with, for example, waste containers, fuel cladding, packaging containers, transport coverings for all land, air, and water vessels, and nuclear waste clean-up.

Article titled "Thin films of synthetic melanin" by S. N. Deziderio et al. published in Journal of Non-Crystalline Solids, 2004, 338-340, pp 634-638 reports a new synthetic route to melanin, using different organic solvents, namely dimethyl sulfoxide and N,N-dimethylformamide. Contrary to conventional water based melanin, thin films can be made with organic solvents. Thin films were made either by room temperature solvent evaporation (casting) or using spin coating.

Article titled "Thermooxidativestabilization of polymers using natural and synthetic melanins" by Kadhiravan Shanmuganathan et al. published in Macromolecules, 2011, 44 (24), pp 9499-9507 reports melanin is a biopolymer well-known for its intriguing chemical structure and physiological functions including photoprotection, radical scavenging, and metal-ion chelation. The potential of natural and synthetic melanins as thermal stabilizers for common polymers by evaluating the addition of melanin to several model polymers with well-known degradation pathways. When added to poly(methyl-methacrylate) (PMMA) in very low amounts (0.55 wt %), synthetic melanin-like polymers significantly altered the radical-initiated chain scission of PMMA and caused a dramatic increase (by about 50-90° C.) in its onset decomposition temperature in both inert and air atmospheres.

U.S. Pat. No. 8,512,685 discloses aqueous hair care compositions which provide hair styling, hair lightening and hair conditioning benefits. The compositions comprise a stabilized oxidative compound, a film-forming hair care polymer, a cationic hair care polymer, and water. Polymer is quaternized hydroxyethylcellulose.

Article titled "Synthesis and characterization of melanin in DMSO" by Bronze-Uhle, Erika S. et al. published in Journal of Molecular Structure, Volume 1047, p. 102-108 reports a comparative study of the structural characteristics of synthetic melanin derivatives obtained by oxidation of L-DOPA in H2O and DMSO. The results suggest that sulfonate groups (—SO2CH3) from the oxidation of DMSO, are incorporated into melanin, which confers protection to the phenolic hydroxyl group present in its structure. The solubility of D-melanin in DMSO is attributed to the presence of these groups. When D-melanin is left in air for long time periods, the sulfonate groups leave the structure, and an insoluble compound is obtained. NaOH and water have been used, in order to accelerate the release of the sulfonate groups attached to D-melanin Article titled "Fast and facile dissolution of cellulose with tetrabutylphosphonium hydroxide containing 40 wt % water" by Mitsuru Abe et al. published in Chemical Communications, 2012, 12 reports Tetrabutylphosphonium hydroxide containing 40 wt % water dissolved 20 wt % cellulose at the final concentration within 5 minutes under mild stirring at 25° C.

The solubility of melanin in solvents like DMSO, acetone, methanol, etc., has been reported. However, these solvents fail to dissolve cellulose, silk or other bio-based polymers. This restricts the commercial viability of melanins. While the insolubility of all types of natural melanins has limited chemical analysis, heterogeneity in structure has made X-ray or neutron scattering studies challenging. Therefore, there is need to find common solvents for cellulose, silk as well as melanin. Accordingly, the present invention helps to incorporate melanin into bio-based polymers at a molecular level, enhancing its properties.

OBJECTIVE OF THE INVENTION

Main objective of the present invention is to provide a process for preparing a homogeneous solution of a polymer and melanin.

Another objective of the present invention is to provide a process for the preparation of fibers and films from said homogeneous solution of a polymer and melanin.

SUMMARY OF THE INVENTION

Accordingly, the present invention provides a process for preparing a homogeneous solution of a polymer and melanin comprising the steps of:

a) dissolving a polymer in tetrabutylammonium hydroxide (TBAH) under continuous vortex mixing for a time period ranging from 1 to 2 hr to obtain a mixture;
b) dissolving melanin in tetrabutylammonium hydroxide (TBAH) under continuous vortex mixing for a time period ranging from 1 to 2 hr followed by mixing with the solution of step (a) to obtain a homogenous solution.

In a preferred embodiment, the homogeneous solution affords composite films, fibers, coatings and shaped forms.

In another preferred embodiment, said melanin is selected from natural or synthetic source and is solubilised using tetrabutylammonium hydroxide (TBAH) or tetrabutylphosphonium hydroxide.

In an embodiment, the present invention provides a process for preparation of fibers from said homogeneous solution comprising extruding said homogeneous solution at a flow rate of 0.01 ml/min in a water bath and rolling on to a spool followed by drying the fibers at a temperature ranging from 30° C. to 40° C. for a time period ranging from 4 to 6 hrs under air convection to afford said fibres.

In a preferred embodiment, said melanin is selected from natural or synthetic source and said polymer is selected from the group consisting of cellulose, silk or other natural polysaccharides and proteins.

In another preferred embodiment, said polymer is selected from the group consisting of cellulose, silk or other natural polysaccharides and proteins.

In still another preferred embodiment, the melanin has a concentration in the range of 0.1 to 1 wt % in TBAH and the polymer has a concentration in the range of 1 to 10 wt % in TBAH.

In still yet another preferred embodiment, the concentration of polymer in said homogeneous solution is in the range of 95 to 99 wt % and melanin is in the range of 1 to 5 wt %.

In still yet another preferred embodiment, said homogeneous solution shows antibacterial activity against gram positive and gram negative bacteria.

In still yet another preferred embodiment, said homogeneous solution is useful for the removal of dyes from effluents.

In yet still another preferred embodiment, said homogeneous solution is used for free radical scavenging having potential applications in chemical waste treatment.

In yet still another preferred embodiment, said homogeneous solution is used for metal-ion chelation having potential applications in chemical waste treatment.

In another preferred embodiment, the fibres are prepared from the cellulose/melanin homogeneous solution by wet spinning method wherein in said method, 1-10 wt % solution of cellulose/melanin homogeneous solution (10:1 w/w) in TBAH is used and water is used as a precipitating bath.

In still another embodiment, the present invention provides a process for the preparation of films from said homogeneous solution comprising the steps of:
a) dissolving a polymer in tetrabutylammonium hydroxide (TBAH) under continuous vortex mixing for a time period ranging from 1 to 2 hrs to obtain a solution;
b) dissolving melanin in tetrabutylammonium hydroxide (TBAH) under continuous vortex mixing for a time period ranging from 1 to 2 hrs followed by mixing with the solution of step (a) to obtain a homogenous solution;
c) casting the homogenous solution of step (b) in Teflon petridishes and following the two step drying procedure.

In a preferred embodiment, the two step drying procedure comprises keeping the film for drying at temperature from 25° C. to 30° C. in a hood and further drying in a vacuum oven for 8 to 10 hours at 50° C. to 60° C.

In another embodiment, the present invention provides a product comprising a homogeneous solution of a polymer and melanin, wherein said homogeneous solution is prepared by the process of the present invention.

In still another embodiment, the present invention provides a composition comprising a homogeneous solution of a polymer and melanin, wherein said homogeneous solution is prepared by process of the present invention.

DETAILED DESCRIPTION OF THE INVENTION

Figure 1:
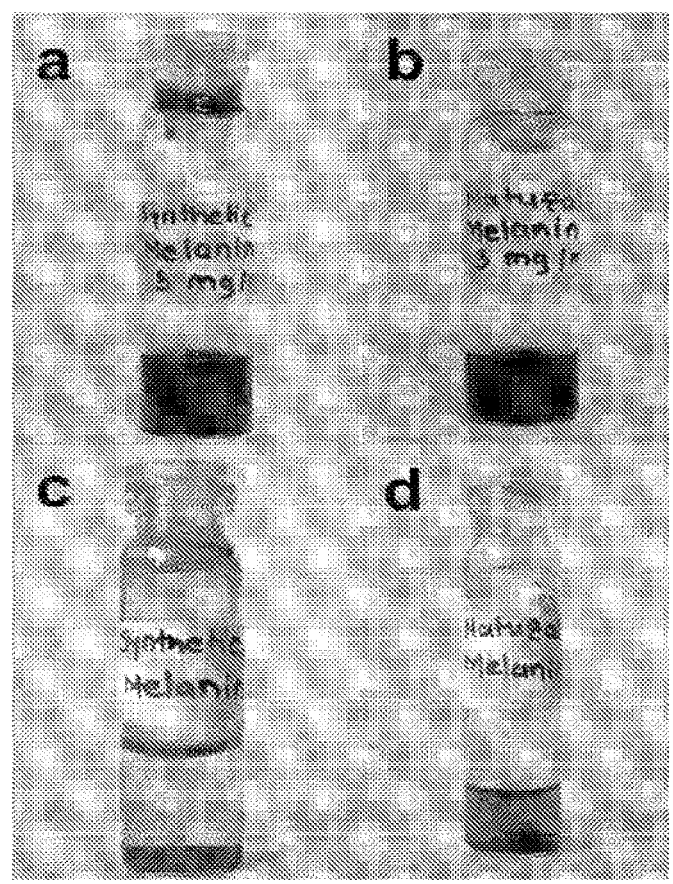
FIG. 1: a) synthetic melanin in TBAH (5 mg/mL); b) natural melanin in TBAH (3 mg/mL); c) synthetic melanin in water (5 mg/mL); d) natural melanin in water (3 mg/mL).

The invention will now be described in detail in connection with certain preferred and optional embodiments, so that various aspects thereof may be more fully understood and appreciated.

The present invention provides a process for preparing a homogeneous solution of a polymer and melanin comprising the steps of:
a) dissolving a polymer in tetrabutylammonium hydroxide (TBAH) under continuous vortex mixing for a time period ranging from 1 to 2 hr to obtain a solution;
b) dissolving melanin in tetrabutylammonium hydroxide (TBAH) under continuous vortex mixing for a time period ranging from 1 to 2 hr followed by mixing with the solution of step (a) to obtain a homogenous solution.

In a preferred embodiment, said homogenous solution affords composite films, fibers, coatings and shaped forms.

In another preferred embodiment, said melanin is selected from natural or synthetic source and is solubilised using tetrabutylammonium hydroxide (TBAH) or tetrabutylphosphonium hydroxide.

In an embodiment, the present invention provides a process for preparation of fibers from said homogeneous solution comprising extruding said homogeneous solution at a flow rate of 0.01 ml/min in a water bath and rolling on to a spool followed by drying the fibers at a temperature ranging from 30° C. to 40° C. for the a period ranging from 4 to 6 h under air convection to afford said fibers.

In a preferred embodiment, said melanin is selected from natural or synthetic source and said polymer is selected from the group consisting of cellulose, silk or other natural polysaccharides and proteins.

In another preferred embodiment, said polymer is selected from the group consisting of cellulose, silk or other natural polysaccharides and proteins.

In still another preferred embodiment, the melanin has a concentration in the range of 0.1 to 1 wt % in TBAH and the polymer has a concentration in the range of 1 to 10 wt % in TBAH.

In still yet another preferred embodiment, the concentration of polymer in said homogeneous solution is in the range of 95 to 99 wt % and melanin is in the range of 1 to 5 wt %.

In still yet another preferred embodiment, said homogeneous solution shows antibacterial activity against gram positive and gram negative bacteria.

In still yet another preferred embodiment, said homogeneous solution is useful for the removal of dyes from effluents.

In yet still another preferred embodiment, said homogeneous solution is used for free radical scavenging having potential applications in chemical waste treatment.

In yet still another preferred embodiment, said homogeneous solution is used for metal-ion chelation having potential applications in chemical waste treatment.

In another preferred embodiment, said fibers are prepared from the cellulose/melanin homogeneous solution by wet spinning method, wherein in said method 1-10 wt % solution of cellulose/melanin homogeneous solution (10:1 w/w) in TBAH is used and water is used as a precipitating bath.

In another embodiment, the present invention provides a process for the preparation of films from said homogeneous solution comprising the steps of:
 a) dissolving a polymer in tetrabutylammonium hydroxide (TBAH) under continuous vortex mixing for the time period ranging from 1 to 2 hr to obtain a solution;
 b) dissolving melanin in tetrabutylammonium hydroxide (TBAH) under continuous vortex mixing for a time period ranging from 1 to 2 hr followed by mixing with the solution of step (a) to obtain a homogenous solution;
 c) casting the homogenous solution of step (b) in Teflon petridishes and following the two step drying procedure.

In a preferred embodiment, the two step drying procedure comprises keeping the film for drying at temperature from 25° C. to 30° C. in a hood and further drying in q vacuum oven for 8 to 10 hours at 50° C. to 60° C.

In another embodiment, the present invention provides a product comprising a homogeneous solution of a polymer and melanin, wherein said homogeneous solution is prepared by the process of the present invention.

In still another embodiment, the present invention provides a composition comprising a homogeneous solution of a polymer and melanin, wherein said homogeneous solution is prepared by the process of the present invention.

Figure 2:
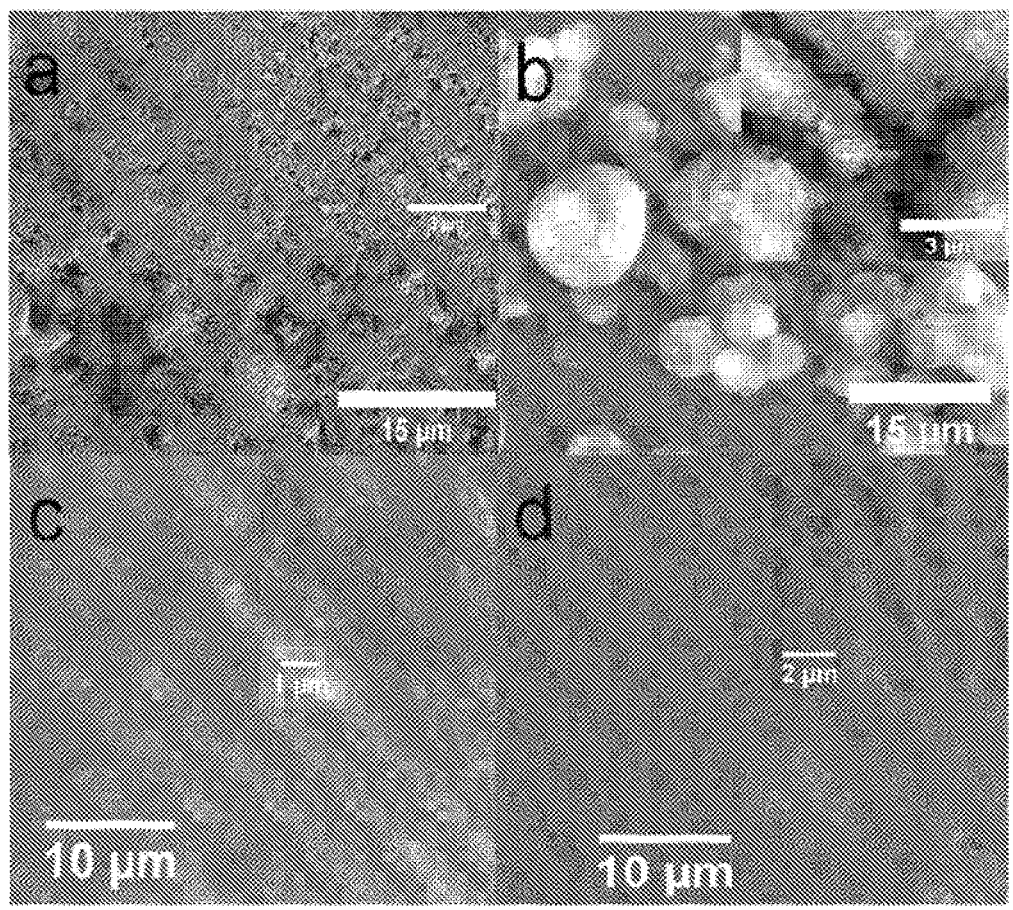
FIG. 2: SEM images of a) synthetic melanin in water, b) natural melanin in water, c) synthetic melanin in TBAH and precipitated in acetone; d) natural melanin in TBAH and precipitated in acetone.

Both natural melanin (melanin derived from Sepia *Officinalis*) and synthetic melanin derived by auto-oxidation of 3,4-dihydroxy-L-phenylalanine (DOPA melanin) yielded stable solutions in TBAH by simple vortex mixing and 15 minutes of ultrasonication. FIGS. 1a and 1b shows the images of the solutions that are prepared and left to rest for a week. Once prepared, the solutions are stable for several weeks. It is important to note that natural and synthetic melanin when subject to vortex mixing and ultrasonication in water also resulted in dispersions. However, the dispersions are unstable and the melanin particles settled down within an hour (FIGS. 1c and 1d). This indicates that in TBAH, melanins are solvated and not merely dispersed by the shear forces during vortex mixing and ultrasonication. The difference may also be observed clearly in the SEM images. Synthetic melanin-water dispersions drop casted on a Si wafer forms a connected sheet but the structure is granular and individual melanin particles can be clearly seen (FIG. 2). However, synthetic melanin solutions in TBAH, when lyophilized and regenerated in acetone form a smooth film, where the granular structure and individual melanin particles could not be observed.

Natural melanin also displayed similar behavior. Since natural melanin is relatively intractable as compared to synthetic melanin, dispersions in water when drop casted on Si wafer do not form a continuous sheet. Rather discrete particles of several microns were observed. However, when natural melanin was dissolved in TBAH and regenerated, they form a continuous film. This suggests both natural and synthetic melanins are solvated in TBAH.

Figure 3:
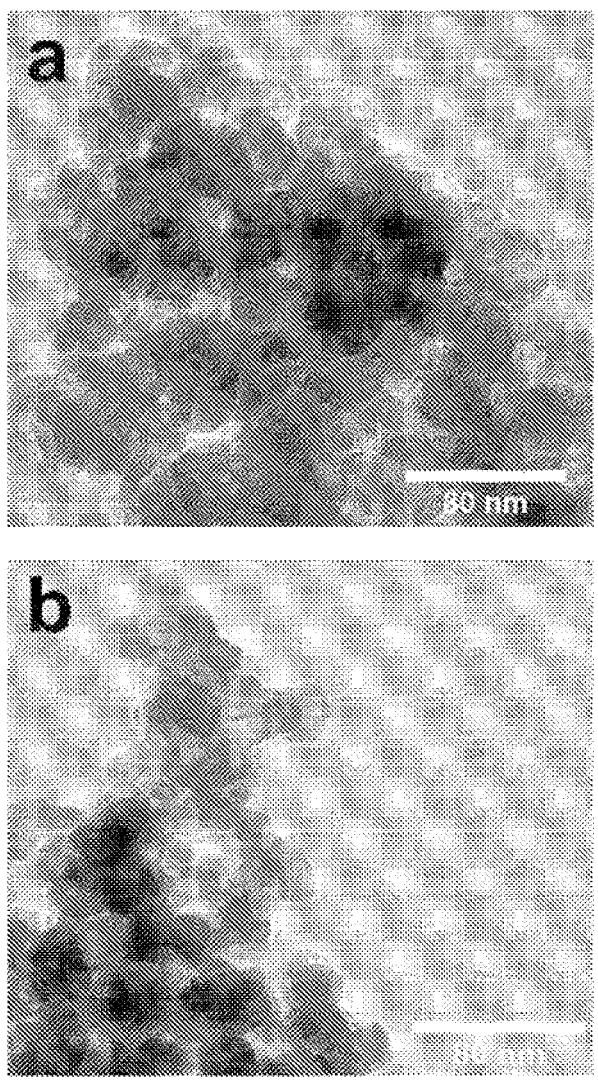
FIG. 3: Transmission electron microscopy images of a) synthetic melanin in TBAH; b) natural melanin in TBAH

The natural and synthetic melanins yield stable solutions in TBAH suggests that TBAH disrupts the secondary structure of melanin leaving behind the primary protomolecules intact. TEM images of 0.01 wt/v % synthetic and natural melanin solutions in TBAH drop casted on a copper grid revealed such intact planar sheets in a de-stacked configuration (FIG. 3). The sheets are uniform in size (around 20 nm) and shape and similar for both natural and synthetic melanins. Interestingly even after solubilisation in TBAH, the same broad band monotonous optical absorbance behavior is retained, which implies that the photophysical properties of melanin originate predominantly from the primary structure (protomolecules) and not the secondary structure (supramolecular organization). The chemical heterogeneity and strong absorbance of melanins makes it difficult to characterize the solutions using standard physical and chemical characterization methods. Hence the dissolution is monitored by optical microscopy imaging of the solutions at different time intervals.

It is observed that synthetic melanins (up to 0.5 wt %) dissolve in TBAH under ambient conditions within an hour as evidenced by the absence of any particles at 40× magnification, whereas in water under similar stirring and sonication, several bigger particles could be seen. Natural melanin (up to 0.3 wt %) takes a longer time (~12 h) to dissolve by vortex mixing and sonication. Further, the dissolution of natural and synthetic melanins in TBAH could be accelerated by microwave irradiation. Natural melanin (10 mg/mL) in TBAH when subjected to microwave radiation (360 W) in 3 sec pulses at a time dissolved in less than 3 minutes. Dissolution of synthetic melanins at similar concentration is easier and faster with microwave radiation and could be achieved with relatively less power.

Optical microscopy of the fibres showed evenly dispersed melanin and no lump or aggregate formation. There is some leeching of melanin observed in the precipitating bath, but none is observed once the fibres are dried out. This may be because of the late skin formation and the swelling that is observed during spinning of the cellulose-TBAH system in water. Robust and continuous fibres could be formed (FIG.

Figure 4:
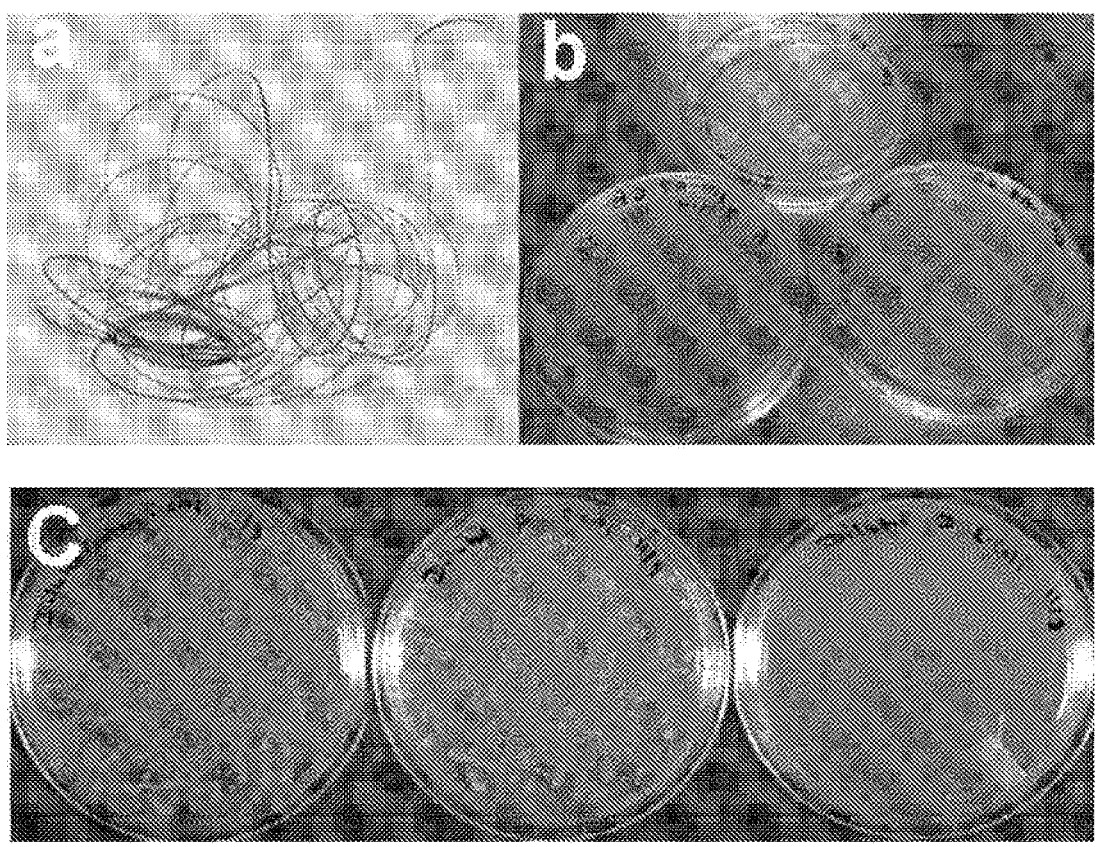
FIG. 4: a) Cellulose/melanin (10:1 w:w) fibres produced by wet spinning cellulose/melanin TBAH solution in water; b) *S. aureus* bacterial growth with control (top), cellulose fibres (bottom left) and cellulose/melanin fibres (bottom right); c) *E. coli* bacterial growth in control (left), cellulose fibres (middle) and cellulose/melanin fibres (right).

4a), which after drying are used for antibacterial tests. While there are a few reports suggesting antimicrobial properties of melanin, it has not been widely employed as an antibacterial agent in films and fibres. The antibacterial efficacy of cellulose/melanin composite fibres is tested against *Staphylococcus aureus* (gram positive) and *Escherichia Coli* (gram negative) using ASTM 2149 test method as shown in FIGS. 4b and 4c, cellulose/melanin composite fibres showed about 80% reduction in bacterial growth for *S. aureus* and almost 100% reduction in bacterial growth for *E. coli*.

Figure 5:
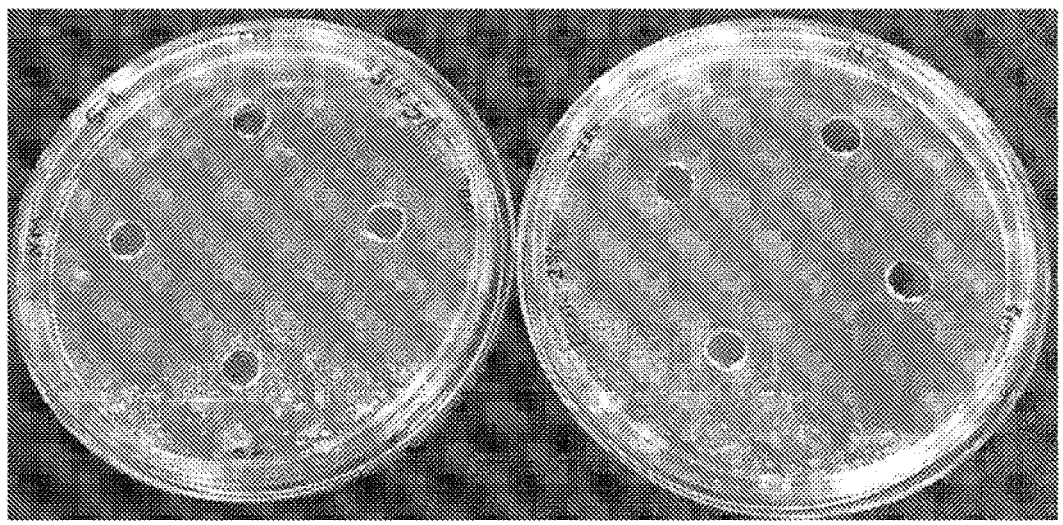
FIG. 5: Well-diffusion tests for evaluating antibacterial properties of (a) 50 µL of 0.05 mg/mL of synthetic melanin in TBAH; (b) 50 µL of 0.03 mg/mL of natural melanin in TBAH; (c) 50 µL of TBAH; and (d) 50 µL of sterile distilled water.

FIG. 5 reveals the antibacterial tests conducted for melanin compositions in TBAH and sterile distilled water as control. All the melanin compositions show complete inhibition of bacterial growth while sterile distilled water control shows excessive bacterial growth around the well.

Figure 6:
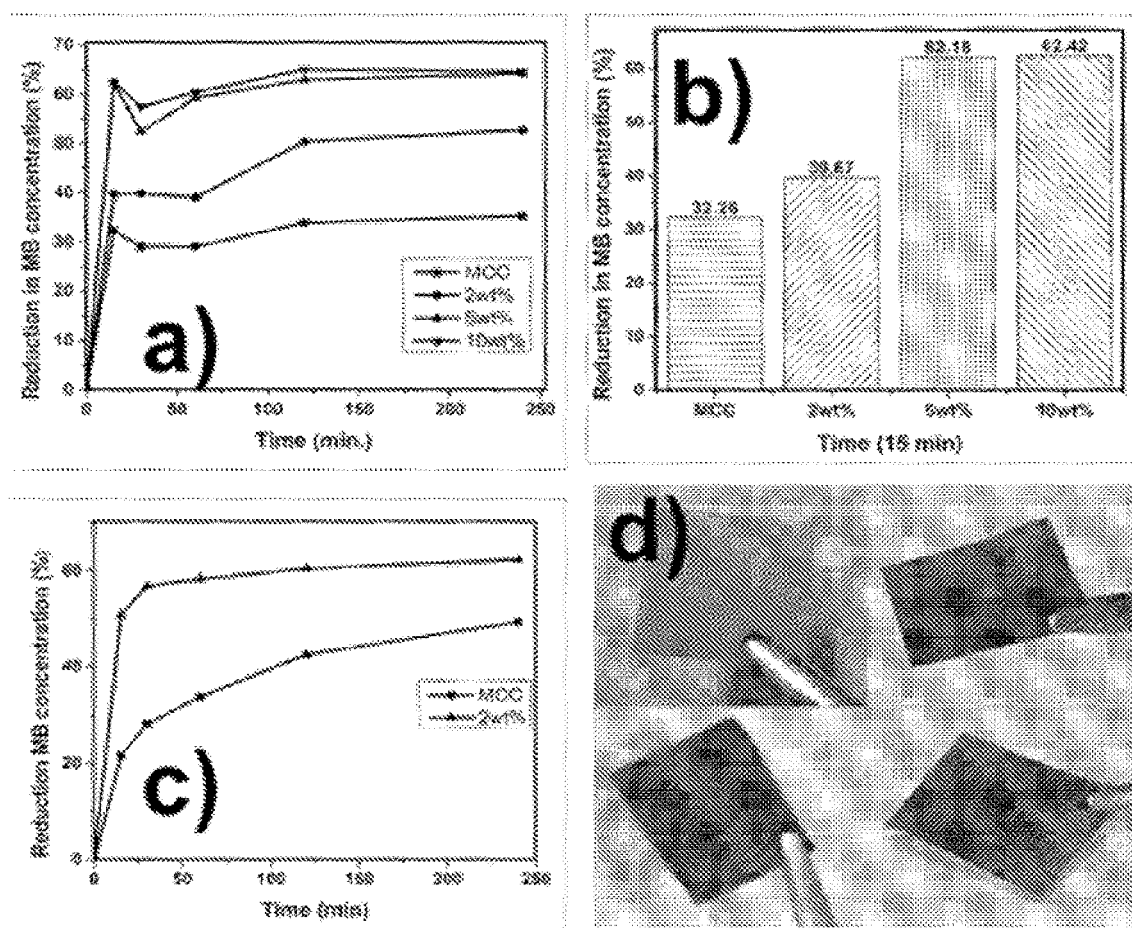
FIG. 6: Kinetics of methylene blue (MB) adsorption on cellulose/melanin; (a and b) % reduction in MB concentration with cellulose/melanin films, c) % reduction in MB concentration with cellulose/melanin fibers, d) digital photographs of cellulose/melanin films: clockwise, neat cellulose, 2, 5 and 10 wt % melanin/cellulose.

A kinetic study was performed to evaluate the ability of fibers and films to adsorb methylene blue dye. As could be seen in FIGS. 6a and 6b, 5 wt % melanin/cellulose composite film showed about 62% reduction in MB concentration within 15 minutes. This is much higher than reported earlier. In case of fibers, similar results were obtained with 2 wt % melanin (FIG. 6c). This could be attributed to the higher specific surface area of fibers as compared to films. It is also very clear that the presence of melanin in small amounts enhances both the kinetics and equilibrium dye uptake as compared to control cellulose fibers. The adsorption of MB could be due to noncovalent interaction viz. π-π stacking, hydrogen bonding and ionic interactions between MB and Melanin.

EXAMPLES

Following examples are given by way of illustration therefore should not be construed to limit the scope of the invention.

Example 1: Synthesis of Melanin

Synthetic melanin was prepared by auto-oxidation of L-DOPA using previously reported method. Briefly 3.0 g of L-DOPA and 4.0 g of benzoyl peroxide were added to 400 mL of DMSO and stirred at the temperature 30° C. After 28 days, reaction mixture was heated at 120° C. to concentrate it. The resultant viscous solution was further precipitated in acetonitrile followed by centrifugation and extraction of the precipitate. Purified product was vacuum dried at 80° C. until a constant weight was obtained.

Example 2: Preparation of Melanin Solutions

To check the solubility of melanins in tetra-n-butylammonium hydroxide (TBAH), concentrations of Sepia (natural) melanin and synthetic melanin ranging from 0.3 w/v % to 0.5 w/v % were prepared in 5 ml TBAH. These solutions, except the first readings at 5 min, were subjected to 15 min sonication at the temperature 30° C., followed by vortex mixing till the point of observation. 20 µl samples were taken after the first 5 min and later at every hour for observation under the optical microscope. The experiment was continued for 12 hr and maximum solubility was determined by optical microscopy. A parallel study was done with the same concentrations, conditions and sampling intervals with DI water as a solvent. These samples were considered as control. Samples that showed maximum solubility were precipitated in excess of DI water and acetone. The results from the optical microscopy were analyzed using ImageJ analysis software.

Example 3: Preparation of Samples for TEM

The samples that had been dissolved were diluted to a concentration of 0.01 w/v % in TBAH and immediately drop casted onto TEM grids. The grids were subjected to vacuum drying at 60° C., −720 mm Hg for 24 hr.

Example 4: Preparation of Samples for SEM

Solutions with maximum solubility in TBAH were drop casted on Si-wafers, as-is, and subjected to lyophilisation, to remove any water content, prior to observation. Samples with DI water as the secondary phase were drop casted on to Si-wafers and dried at room temperature under constant air convection. Similar protocol was followed for the precipitated samples.

Example 5: Fibre Spinning

For fibre spinning, melanin-TBAH system was incorporated in microcrystalline cellulose (MCC)-TBAH and the solution was extruded using a syringe and a syringe pump. 500 mg MCC, along with 10 mg synthetic melanin was dissolved in 5 ml TBAH, under continuous vortex mixing for 2 h. The solution was extruded using 21 gauge needle at a flow rate of 0.01 ml/min in a DI water bath and later rolled on to a spool manually. The fibres were dried for 4 h at 30° C. under air convection.

Example 6: Antibacterial Tests

The antibacterial properties of cellulose and cellulose/melanin composite fibres were evaluated by ASTM E2149 standard test method, a quantitative antimicrobial test method performed under dynamic contact conditions. Both gram positive (*Staphylococcus aureus*) and gram negative (*Escherichia coli*) were used as test organisms. The incubated test culture in a nutrient broth was diluted (serial diluted) with a sterilized 0.3 mM phosphate buffer (pH 7.2) to give a final concentration of $5 \times 10^3$ colony forming unit (CFU)/ml. This solution was used as a working bacterial dilution. Fibre samples (20 mg) were transferred to a 250 ml Erlenmeyer flask containing 50 ml of the working bacterial dilution. All flasks were capped loosely (capped with cotton plug), placed on the incubator, and shaken for 22 h at 37° C. and 120 rpm using an incubator shaker. After a series of dilutions of the bacterial solutions using the buffer solution, 20 µL of the dilution was plated in nutrient agar (innoculated in nutrient agar petri dishes). The inoculated plates were incubated at 37° C. for overnight and surviving cells were counted. The average values of the duplicates were converted to CFU/ml in the flasks by multiplying by the dilution factor. The antimicrobial activity was expressed in terms of % reduction of the organism after contact with the test specimen compared to the number of bacterial cells surviving after contact with the control. The percentage reduction was calculated using the following equation, $$\% \text{ Reduction} = 100*(B-A)/B$$

Where A and B are the surviving cells (CFU/ml) for the flasks containing test samples (cellulose/melanin) and the control (blank cellulose fibres), respectively, after 22 h contact time. Cellulose/melanin composite fibres show 80-99% reduction in bacterial growth as compared to control cellulose fibres processed using similar protocol.

Example 7: Dye Adsorption Tests

As prepared films and fibers were tested for dye absorption capacity. As reported earlier, 30 ml of MB solution of 2 mg/L concentration was taken in a vial with approximately 30 mg of film/fiber samples and left up to 24 h. Aliquots of samples were collected at specified time intervals (0.25, 0.5, 1, 2, 4 h, 15 h and 24 h) and absorbance was recorded using Agilent 89090A spectrophotometer. All experiments were performed in duplicates and average difference in absorbance converted to concentration using Beer-Lambert's law. % reduction in MB concentration was finally calculated as follows.

$$\% \text{ Reduction}=[MB]_0-[MB]_t/[MB]_0*100$$

Advantages of the Invention

1. This process helps to incorporate melanin into bio-based polymers at a molecular level, enhancing its properties.
2. The composition showed significant decrease in activity of gram positive and gram negative bacteria.
3. The composition showed significant reduction in concentration of methylene blue dye.

We claim:

1. A process for preparing a solution of a polymer and melanin comprising the steps of:
    a. dissolving a polymer in tetrabutylammonium hydroxide (TBAH) solution under continuous vortex mixing for a time period ranging from 1 to 2 hr to obtain a solution;
    b. dissolving melanin in tetrabutylammonium hydroxide (TBAH) solution under continuous vortex mixing for a time period ranging from 1 to 2 hr followed by mixing with the solution of step (a) to obtain a mixed solution, wherein the relative amounts of the polymer and the melanin in the mixed solution are in the range of 95 to 99 weight % and in the range of 1 to 5 weight %, respectively.

2. The process as claimed in claim 1, wherein said mixed solution is used to obtain composite films, fibers, coatings and shaped forms.

3. The process as claimed in claim 2, wherein said fibers are prepared by a process comprising extruding said mixed solution at a flow rate of 0.01 ml/min in a water bath and rolling on to a spool followed by drying the fibers at a temperature ranging from 30° C. to 40° C. for a time period ranging from 4 to 6 h under air convection to obtain said fibers.

4. The process as claimed in claim 1, wherein the melanin is selected from natural or synthetic source and said polymer is selected from the group consisting of cellulose, silk, other natural polysaccharides, and proteins.

5. The process as claimed in claim 1, wherein the melanin has a concentration of in the range of 0.1 to 1 weight % in the TBAH solution of the step (b) and the polymer has a concentration in the range of 1 to 10 weight % in the TBAH solution of the step (a).

6. The process as claimed in claim 1, wherein said mixed solution shows antibacterial activity against gram positive and gram negative bacteria.

7. The process as claimed in claim 1, wherein said mixed solution is used in removal of dyes from effluents.

* * * * *